United States Patent
Bombardelli

(10) Patent No.: US 10,583,162 B2
(45) Date of Patent: Mar. 10, 2020

(54) COMPOSITIONS USEFUL IN THE PREVENTION AND/OR TREATMENT OF OSTEOARTICULAR INFLAMMATION AND PAIN AND CARTILAGE DAMAGE

(71) Applicant: Indena S.P.A., Milan (IT)

(72) Inventor: Ezio Bombardelli, Gropello Cairoli (IT)

(73) Assignee: Indena S.P.A., Milan (IT)

( * ) Notice: Subject to any disclaimer, the term of this patent is extended or adjusted under 35 U.S.C. 154(b) by 0 days.

(21) Appl. No.: 16/313,202

(22) PCT Filed: Jun. 28, 2017

(86) PCT No.: PCT/EP2017/066002
§ 371 (c)(1),
(2) Date: Dec. 26, 2018

(87) PCT Pub. No.: WO2018/002144
PCT Pub. Date: Jan. 4, 2018

(65) Prior Publication Data
US 2019/0151396 A1   May 23, 2019

(30) Foreign Application Priority Data

Jun. 29, 2016 (IT) .................. 102016000067621

(51) Int. Cl.
| | | |
|---|---|---|
| A61K 36/00 | (2006.01) | |
| A61K 36/87 | (2006.01) | |
| A61K 36/758 | (2006.01) | |
| A61K 36/9068 | (2006.01) | |
| A61K 31/7008 | (2006.01) | |
| A61K 36/28 | (2006.01) | |
| A61K 36/63 | (2006.01) | |
| A61K 36/899 | (2006.01) | |
| A61K 36/185 | (2006.01) | |
| A61K 31/235 | (2006.01) | |
| A61P 19/02 | (2006.01) | |
| A61K 9/20 | (2006.01) | |
| A61K 9/48 | (2006.01) | |
| A61K 31/047 | (2006.01) | |
| A61K 31/05 | (2006.01) | |
| A61K 31/16 | (2006.01) | |
| A61K 31/194 | (2006.01) | |
| A61K 31/7048 | (2006.01) | |
| A61K 36/61 | (2006.01) | |
| A61K 47/24 | (2006.01) | |

(52) U.S. Cl.
CPC .............. *A61K 36/87* (2013.01); *A61K 9/20* (2013.01); *A61K 9/4866* (2013.01); *A61K 9/4875* (2013.01); *A61K 31/047* (2013.01); *A61K 31/05* (2013.01); *A61K 31/16* (2013.01); *A61K 31/194* (2013.01); *A61K 31/235* (2013.01); *A61K 31/7008* (2013.01); *A61K 31/7048* (2013.01); *A61K 36/185* (2013.01); *A61K 36/28* (2013.01); *A61K 36/61* (2013.01); *A61K 36/63* (2013.01); *A61K 36/758* (2013.01); *A61K 36/899* (2013.01); *A61K 36/9068* (2013.01); *A61K 47/24* (2013.01); *A61P 19/02* (2018.01)

(58) Field of Classification Search
None
See application file for complete search history.

(56) References Cited

U.S. PATENT DOCUMENTS

| | | |
|---|---|---|
| 2012/0244087 A1 | 9/2012 | Trivedi et al. |
| 2014/0014344 A1 | 1/2014 | Daussin |

FOREIGN PATENT DOCUMENTS

| | | |
|---|---|---|
| GB | 2403405 A | 1/2005 |
| WO | 2010123179 A1 | 10/2010 |
| WO | 2011048221 A1 | 4/2011 |
| WO | 2012013551 A1 | 2/2012 |
| WO | 2012060884 A1 | 5/2012 |
| WO | 2015124616 A1 | 8/2015 |

OTHER PUBLICATIONS

Jayaraj P., et al., "The genus *spilanthes* ethnopharmacology, phytochemistry and pharmacological properties: A review", Advances in Pharmacological Sciences, vol. 2013, Jan. 1, 2013, pp. 510298-1-23.
Pavelka K., "Diacerein: benefits, risks and place in the management of ostearthritis. An opinion-based report from ESCEO", Drugs & Aging, vol. 33, No. 2, Feb. 2016, pp. 75-85.
Search Report and Written Opinion dated Sep. 15, 2017 for PCT/EP2017/066002.

*Primary Examiner* — Qiuwen Mi
(74) *Attorney, Agent, or Firm* — Silvia Salvadori, P.C.; Silvia Salvadori

(57) ABSTRACT

The present invention relates to compositions comprising: a) a *Vitis vinifera* extract in free form or in the form of a complex with phospholipids, or a *Punica granatum* extract; and b) a lipophilic extract of *Zingiber officinale*; and c) a lipophilic extract obtained from plants containing polyunsaturated fatty acid isobutylamides selected from the group consisting of *Echinacea* spp. extract or *Zanthoxylum* spp. extract or *Acmella oleracea* (or *Spilanthes oleracea*) extract; and d) an unsaponifiable fraction of olive oil and/or corn oil; or e) N-acetyl glucosamine; or f) diacerein; and their use in the prevention and/or treatment of osteoarticular inflammation and pain, and cartilage damage.

17 Claims, No Drawings

COMPOSITIONS USEFUL IN THE PREVENTION AND/OR TREATMENT OF OSTEOARTICULAR INFLAMMATION AND PAIN AND CARTILAGE DAMAGE

This application is a U.S. national stage of PCT/EP2017/066002 filed on 28 Jun. 2017, which claims priority to and the benefit of Italian Application No. 102016000067621 filed on 29 Jun. 2016, the contents of which are incorporated herein by reference in their entireties.

TECHNICAL FIELD OF INVENTION

The present invention relates to compositions comprising a *Vitis vinifera* extract in free form or in the form of a complex with phospholipids, or a *Punica granatum* extract; a lipophilic extract of *Zingiber officinale*; and an extract obtained from plants containing polyunsaturated fatty acid isobutylamides; combined with an unsaponifiable fraction of olive oil and/or corn oil, or with N-acetyl glucosamine or diacerein; which are useful in the prevention and/or treatment of osteoarticular inflammation and pain, and cartilage damage.

PRIOR ART

Peripheral inflammations, especially those associated with joint wear, osteoarthritis, rheumatoid arthritis and psoriatic arthritis, are among the main causes of disability in middle-aged and elderly persons.

Said disorders have very different etiologies. In some cases they are autoimmune disorders, in others disorders due to mechanical wear on the main joints subject to constant stress, especially when the individual is overweight, and to dysmetabolic biochemical changes associated with the aging process. The biochemical changes involve altered proteoglycan synthesis and overproduction of cytokines, which maintain the inflammation.

Osteoarthritis (OA) is a degenerative disease characterised by synovial alterations and destruction of joint cartilage and subchondral bone. This condition affects and debilitates about 10% of the population between 65 and 73 years old.

Treatments for rheumatoid arthritis and psoriatic arthritis exist, but they are unpleasant and debilitating, and no specific treatment currently exists for osteoarthritis.

The first-line medicaments are still non-steroidal anti-inflammatory drugs (NSAIDs) with a symptomatic action, which are often poorly tolerated by patients.

The classic anti-inflammatories, from high-dose aspirin to those of the latest generation, necessarily involve lengthy treatments and serious side effects, especially at gastric level and also, as recently discovered, at cardiac and vascular level.

Infiltrations of hyaluronic acid into the joint or infiltrations of autologous stem cells are used to reduce joint damage, and therefore its symptoms.

The consumption of OA supplements has grown exponentially in recent years. Said supplements are substantially preparations based on chondroitin sulphate, glucosamine or derivatives thereof, diacerein and unsaponifiable fractions of some oils, and are always used in combination with major drugs to reduce pain.

All these products, and numerous other products of plant origin, are used, but one of the problems involved is their low level of pain reduction, forcing patients to use the above-mentioned painkillers, which in the last analysis reduce the benefit of treatment designed to recover metaphyseal cartilage.

New osteoarthritis products are therefore needed which improve the tolerability of the treatment with no loss of therapeutic efficacy.

Lipophilic extracts derived from medicinal plants, such as extracts of *Zingiber officinale, Echinacea* spp, *Zanthoxylum bungeanum, piperitum* or *armatum* or *Acmella oleracea* (or *Spilanthes oleracea*), applied topically or systemically, are known to perform an anti-inflammatory and analgesic action associated with the presence of polyunsaturated fatty acid isobutylamides, which are ligands of cannabinoid receptors CB1 and CB2 and vanilloids, and in particular act as TRPV1 agonists. However, their anti-inflammatory and analgesic activity is insufficient to solve the osteoarticular problem, as they do not act on the final causes leading to the onset of the disorder.

It is known from pharmacology that molecules with antiradical and protease-inhibiting activity such as hyaluronidase, collagenase and elastase, together with interleukin 1 and 6 inhibitors, improve the joint function, provided that they reach the target organ.

The data reported in the clinical literature suggest that some substances, if taken for sufficiently long times, may play a part in preventing joint damage if the general pain treatment conditions allow them to be used for sufficiently long times, without having to interrupt the treatment prematurely due to the onset of side effects.

There is consequently still a need to identify alternative products useful in the prevention and/or treatment of osteoarticular inflammation and pain and damage to joint cartilage.

SUMMARY OF THE INVENTION

The present invention relates to compositions comprising:
a) a *Vitis vinifera* extract in free form or in the form of a complex with phospholipids, or a *Punica granatum* extract; and
b) a lipophilic extract of *Zingiber officinale*; and
c) a lipophilic extract obtained from plants containing polyunsaturated fatty acid isobutylamides selected from the group consisting of *Echinacea* spp. extract or *Zanthoxylum* spp. extract or *Acmella oleracea* (or *Spilanthes oleracea*) extract; and
d) an unsaponifiable fraction of olive oil and/or corn oil; or
e) N-acetyl glucosamine; or
f) diacerein.

The present invention also relates to the use of said compositions in the prevention and/or treatment of osteoarticular inflammation and pain, and cartilage damage.

DETAILED DESCRIPTION OF THE INVENTION

It has now surprisingly been found that compositions comprising a *Vitis vinifera* extract in free form or in the form of a complex with phospholipids, or a *Punica granatum* extract; a lipophilic extract of *Zingiber officinale*; and an extract obtained from plants containing polyunsaturated fatty acid isobutylamides; combined with an unsaponifiable fraction of olive oil and/or corn oil, or with N-acetyl glucosamine, or with diacerein, are effective in the prevention and/or treatment of osteoarticular inflammation and pain, and damage caused by wear on the joint sockets, especially the particularly exposed skeletal parts.

The present invention relates to compositions comprising:

a) a *Vitis vinifera* extract in free form or in the form of a complex with phospholipids, or a *Punica granatum* extract; and b) a lipophilic extract of *Zingiber officinale*; and c) a lipophilic extract obtained from plants containing polyunsaturated fatty acid isobutylamides selected from the group consisting of *Echinacea* spp. extract or *Zanthoxylum* spp. extract or *Acmella oleracea* (or *Spilanthes oleracea*) extract; and d) an unsaponifiable fraction of olive oil (*Olea europaea*) and/or corn oil; or e) N-acetyl glucosamine; or f) diacerein.

The *Punica granatum* extract is preferably obtained from ripe fruit by extraction with ethanol and purification on absorbing resins. The extract may also be characterised by a 40% w/w punicalagin content.

The *Vitis vinifera* extract is preferably obtained from the seeds, as described in GB 15441469, EP 2189062 or EP 1909750.

According to the present invention, "*Vitis vinifera* extract in the form of a complex with phospholipids" means the product prepared according to EP 0275224.

The lipophilic extract of *Zingiber officinale* is preferably obtained from the roots and rhizomes. The extract also preferably has a high gingerol and shogaol content; a *Zingiber officinale* extract containing 30% w/w gingerols and shogaols, preferably 25% w/w gingerols, is particularly preferred.

*Echinacea* spp., *Zanthoxylum* spp. or *Acmella oleracea* (or *Spilanthes oleracea*) extracts may be obtained by extraction with aprotic solvents from the fruit or parts of the respective plants normally used for extraction.

Lipophilic extracts of *Echinacea* spp., *Zanthoxylum* spp., *Zingiber officinale* and *Acmella oleracea* may be obtained by extraction from the roots or rhizomes with alcohols, ketones or aliphatic ethers or, preferably, with carbon dioxide under supercritical conditions. The *Echinacea* spp. extract can be prepared according to EP0464298 A1 (page 2 lines 1-52, and from page 5 line 45 to page 6 line 7). The lipophilic extract of *Zanthoxylum* spp. can be prepared according to WO 00/02570 A1 (from page 1 line 26 to page 2 line 13, and from page 4 line 28 to page 7 line 21). The lipophilic extract of *Zanthoxylum* spp. is preferably a *Zanthoxylum bungeanum* or *piperitum* extract, and is more preferably a standardised extract containing 25% w/w isobutylamides.

The unsaponifiable fraction of olive oil may be prepared by saponifying olive-pomace oils, also containing the oil that can be extracted from the drupes, and isolating the unsaponifiable fraction from triterpenes, sterols, long-chain branched or unbranched alcohols, and squalene. By-products of *Olea europaea* production are preferably used. The terpene and polyalcohol content ranges between 40 and 90% w/w, and is preferably 60% w/w.

According to a preferred aspect of the invention, the compositions comprise:

a) a *Vitis vinifera* extract in free form or in the form of a complex with phospholipids, or a *Punica granatum* extract;

b) a lipophilic extract of *Zingiber officinale;* c) a lipophilic extract of *Echinacea* spp., *Zanthoxylum* spp. or *Acmella oleracea* (or *Spilanthes oleracea*), preferably a *Zanthoxylum* spp. extract, and even more preferably a *Zanthoxylum bungeanum* extract; and d) an unsaponifiable fraction of olive oil (*Olea europaea*).

The compositions according to the invention for oral administration may comprise per dosage unit:

a) a *Vitis vinifera* extract in free form or in the form of a complex with phospholipids, or a *Punica granatum* extract, in amounts ranging from 50 to 1000 mg, preferably 200 mg;

b) a lipophilic extract of *Zingiber officinale* in amounts ranging from 10 to 80 mg, preferably 50 mg;

c) a lipophilic extract of *Zanthoxylum* spp. in amounts ranging from 1 to 50 mg, preferably 20 mg, or, alternatively, a lipophilic extract of *Echinacea* spp. or *Acmella oleracea* (or *Spilanthes oleracea*) in amounts ranging from 5 to 50 mg, preferably 10 mg;

d) an unsaponifiable fraction of olive oil (*Olea europaea*) in amounts ranging from 50 to 500 mg, preferably 150 mg.

According to a further aspect of the invention, the unsaponifiable fraction in the compositions may be replaced by N-acetyl glucosamine in amounts ranging from 50 to 500 mg, preferably 150 mg, or by diacerein in amounts ranging from 20 to 200 mg, preferably 50 mg.

According to a particularly preferred aspect, the compositions for oral administration comprise, per dosage unit, 200 mg of *Vitis vinifera* extract, complexed with phospholipids; 50 mg of lipophilic extract of *Zingiber officinale* containing 30% w/w gingerols and shogaols; 10 mg of lipophilic extract of *Zanthoxylum* spp.; and 100 mg of unsaponifiable fraction of olive oil (*Olea europaea*) or 150 mg of N-acetyl glucosamine or 50 mg of diacerein.

According to a preferred aspect, the compositions according to the invention for topical administration may comprise:

a) a *Vitis vinifera* extract complexed with phospholipids in amounts ranging from 0.1 to 2.5% w/w, preferably 1% w/w;

b) a lipophilic extract of *Zingiber officinale* in amounts ranging from 0.1 to 1% w/w, preferably 0.5% w/w;

c) a lipophilic extract of *Zanthoxylum* spp. in amounts ranging from 0.1 to 1% w/w, preferably 0.5% w/w;

d) an unsaponifiable fraction of olive oil (*Olea europaea*) in amounts ranging from 0.1 to 1 w/w, preferably 0.5 w/w.

The present invention also relates to the use of said compositions in the prevention and/or treatment of osteoarticular inflammation and pain and cartilage damage.

The compositions have proved useful in the prevention and/or treatment of osteoarticular inflammation and pain. They act on the synthesis or inhibition of proteoglycan hydrolysis in metaphyseal cartilage and synovial fluids.

The compositions according to the invention have proved useful in the prevention and/or treatment of peripheral pain of all kinds, such as diabetic neuropathy, neuropathic pain induced by chemotherapy, especially that caused by platinum derivatives, muscle pain of various origins, and inflammatory states such as skin inflammations of various origins.

The compositions have proved particularly effective in the treatment of osteoarticular inflammation and pain, in particular peripheral and systemic pain, especially in the small and large joints. Their effect on the large joints, such as the knee and the femoral sockets, which are essential for walking, is particularly important.

The compositions according to the invention have exhibited potent, long-lasting analgesic and anti-inflammatory activity, even after discontinuance of the treatment, unlike steroidal and non-steroidal anti-inflammatory drugs.

The compositions according to the invention reinstate the physiological restoration of the joint matrices, and are therefore useful to reduce invasive treatments, such as infiltrations of lubricants or steroids into the joint.

The ingredients of the composition according to the invention, when taken individually, exhibited modest efficacy, whereas when suitably according to the invention combined they gave rise to a totally different profile in terms of tolerability and efficacy, exhibiting a synergistic effect. The compositions according to the invention are extremely advantageous for the patient because they have an analgesic and anti-inflammatory effect with no major long-term side effects.

Formulations comprising the compositions according to the invention may be obtained by conventional techniques as described, for example, in "Remington's Pharmaceutical Handbook", Mack Publishing Co., N.Y., USA. In particular, the compositions according to the invention may be formulated by techniques conventionally used to formulate plant-based ingredients.

The compositions according to the invention may be administered orally or topically.

Examples of oral formulations are tablets, dragées, soft and hard gelatin capsules, and cellulose capsules.

The compositions according to the invention may preferably be formulated in the form of soft gelatin capsules or emulsions.

The examples below further illustrate the invention.

EXAMPLE 1

Soft gelatin capsules containing the following ingredients were prepared:

| | |
|---|---|
| *Vitis vinifera* extract complexed with phospholipids | 200.00 mg |
| lipophilic extract of *Zingiber officinale* (25% w/w gingerols) | 50.00 mg |
| lipophilic extract of *Zanthoxylum bungeanum* obtained by extraction with $CO_2$, standardised to 25% w/w isobutylamides | 15.00 mg |
| unsaponifiable fraction of *Olea europaea* | 150.00 mg |
| linseed oil | q.s. to 800 mg |

EXAMPLE 2

Soft gelatin capsules containing the following ingredients were prepared:

| | |
|---|---|
| *Punica granatum* extract | 200.00 mg |
| lipophilic extract of *Zanthoxylum piperitum* obtained by extraction with $CO_2$, standardised to 25% w/w isobutylamides | 15.00 mg |
| lipophilic extract of *Zingiber officinale* (25% w/w gingerols) | 50.00 mg |
| N-acetyl glucosamine | 150.00 mg |
| linseed oil | q.s. to 700.00 mg |

EXAMPLE 3

Soft gelatin capsules containing the following ingredients were prepared:

| | |
|---|---|
| *Punica granatum* extract | 200.00 mg |
| lipophilic extract of *Zanthoxylum piperitum* obtained by extraction with $CO_2$, standardised to 25% w/w isobutylamides | 20.00 mg |
| lipophilic extract of *Zingiber officinale* (25% w/w gingerols) | 50.00 mg |
| diacerein | 50.00 mg |
| linseed oil | q.s. to 700.00 mg |

EXAMPLE 4

Soft gelatin capsules containing the following ingredients were prepared:

| | |
|---|---|
| *Vitis vinifera* extract complexed with phospholipids | 250.00 mg |
| lipophilic extract of *Zanthoxylum piperitum* obtained by extraction with $CO_2$, standardised to 25% w/w isobutylamides | 20.00 mg |
| lipophilic extract of *Zingiber officinale* (25% w/w gingerols) | 50.00 mg |
| diacerein | 50.00 mg |
| linseed oil | q.s. to 700.00 mg |

EXAMPLE 5

Test of Activity in Humans

The analgesic activity of a composition according to the invention comprising *Vitis vinifera* extract complexed with phospholipids, lipophilic extract of *Zingiber officinale*, lipophilic extract of *Zanthoxylum piperitum* and an unsaponifiable fraction of *Olea europaea* was compared with the activity of piroxicam and a placebo.

In a blinded study conducted on 180 patients with osteoarthritis, mainly located in the knee, the composition of example 1 was compared with piroxicam and a placebo by conducting a three-month treatment after randomisation, and check-ups on the joint function for six months after discontinuance of the treatment.

At the beginning, the analgesic effect, measured with the Western Ontario and McMaster University Osteoarthritis (WOMAC) scale, was evaluated after 7 days' treatment with two capsules/day of the composition of example 1 vs. two 600 mg capsules of piroxicam or placebo. After the first 7 days, the treatment continued for three months, the analgesic effect being measured once a month.

The two groups treated with the composition of example 1 and piroxicam had a comparable analgesic effect, but the composition of example 1 proved more tolerable, as the treatment of some patients in the group treated with piroxicam had to be discontinued due to evident side effects. In the placebo group there was no improvement, and a tendency to deterioration.

During the third month's treatment, the result of the composition of example 1 vs. the formulation containing piroxicam was −76%+/−28.6% vs. −72%+/−31.4% (P ns), while the placebo result was −25%+/−21%.

After discontinuance of the treatment in the 4th month, the pain worsened in the group treated with piroxicam by −41%+/−38%, and the result further fell to −24%+/−23% in the 5th month, with a very similar score to the placebo group. The composition of example 1 scored −68%+/−26% in the 4th month and −70.06%+/−31% in the 5th month.

In this case, the difference between piroxicam/placebo and the composition of example 1 is highly significant. This result clearly indicates for the composition of example 1 a protective effect on the catabolism of the metaphyseal cartilage, or anyhow restoration of the cartilage. The damage shown on X-ray, where the intra-articular thickness was 2 mm on average in the pathological situation, declined qualitatively, but experimental difficulties prevented a statistical evaluation.

In fact, with the compositions according to the present invention, after improved restoration of the synovial cartilage surface in the patients in the double-blind trial, its efficacy was maintained for a further 6 months after discontinuance of the treatment, whereas the patients treated with the reference compound piroxicam needed to continue the treatment.

EXAMPLE 6

Evaluation of Analgesic Activity in Humans 40 patients suffering from joint disease of the knee with constant pain were randomised and treated with two tablets a day, one in the morning and one in the evening, of the composition of example 4, or a placebo (consisting of the carrier only), or the ingredients of the composition of example 1 added individually to the placebo formulation in amounts equal to those present in the composition of example 4.

Efficacy was scored on an international analogue pain scale with scores from 0 to 10, 10 points indicating maximum pain and 0 the disappearance of pain. The effect was evaluated on the second day after administration of the tablet, in the morning 60 and 120 minutes after treatment.

The results are set out in Table 1 below.

TABLE 1

| Treatment | Pain (scores) at time | | |
| --- | --- | --- | --- |
| | 0 | 60 min. | 120 min. |
| Placebo | 9.3 ± 0.9 | 9.2 ± 1.7 | 9.0 ± 1.7 |
| Composition of example 4 | 9.1 ± 2.1 | 3.6 ± 0.7 | 2.0 ± 1.2 |
| *Zanthoxylum piperitum* extract (25% w/w isobutylamides) | 9.2 ± 1.4 | 7.6 ± 1.1 | 6.9 ± 1.1 |
| *Zingiber officinale* (25% w/w gingerols) | 9.4 ± 1.3 | 8.3 ± 0.9 | 8.9 ± 1.2 |
| Diacerein | 9.1 ± 1.5 | 8.2 ± 0.9 | 7.9 ± 0.8 |
| Phospholipid-complexed *Vitis vinifera* | 9.0 ± 1.3 | 8.3 ± 1.2 | 8.4 ± 1.4 |

EXAMPLE 7

Evaluation of Analgesic Activity in Humans

Table 2 shows the results obtained after treatment for up to three months with the composition of example 3, and for up to six months after the end of the treatment, on the global effect of osteoarthritis on the patients recruited, according to the Karnofsky Scale (J. Clin. Oncology 1984; 2:187-193) for both selection and evaluation of efficacy.

The evaluation was conducted by measuring the distance travelled without pain, and with different degrees of pain, on a treadmill set to 3 Km/h and an inclination of 10%.

80 patients suffering from osteoarthritis of the knee were divided into two groups. After randomisation, one group was treated with the placebo and the other with the composition of example 3. During the treatment, pain was evaluated weekly with WOMAC, and the humoral parameters, which indicate the inflammatory parameters, were evaluated monthly, and they were found to have improved.

TABLE 2

Results of distance travelled on treadmill

| Treatment | Distance travelled at time | | |
| --- | --- | --- | --- |
| | 0 | 1 month | 3 months |
| Placebo | 81.4 metres | 86.3 metres | xx |
| Composition of example 3 | 84.2 metres | 201.3 metres | 390.4 metres |

The distance travelled 6 months after the end of the treatment was 320 m.

xx: patients who left the trial for ethical reasons and were treated with other medicaments.

The invention claimed is:

1. A composition comprising:
   a) an extract of *Vitis vinifera* in free form or in the form of a complex with phospholipids, or an extract of *Punica granatum* in amounts ranging from 50 to 1000 mg;
   b) a lipophilic extract of *Zingiber officinale* in amounts ranging from 10 to 80 mg;
   c) a lipophilic extract of *Zanthoxylum* spp. in amounts ranging from 1 to 50 mg or, alternatively, a lipophilic extract of *Echinacea* spp. or of *Acmella oleracea* in amounts ranging from 5 to 50 mg;
   and
   d) an unsaponifiable fraction of olive oil and/or corn oil in amounts ranging from 50 to 500 mg; or
   e) N-acetylglucosamine in amounts ranging from 50 to 500 mg; or
   f) diacerein in amounts ranging from 20 to 200 mg.

2. The composition according to claim 1, comprising:
   a) an extract of *Vitis vinifera* seeds in free form or in the form of a complex with phospholipids, or an extract of *Punica granatum* in amounts ranging from 50 to 1000 mg; and
   b) a lipophilic extract of *Zingiber officinale* in amounts ranging from 10 to 80 mg; and
   c) a lipophilic extract of *Zanthoxylum* spp. in amounts ranging from 1 to 50 mg or, alternatively, a lipophilic extract of *Echinacea* spp. or of *Acmella oleracea* in amounts ranging from 5 to 50 mg; and
   d) an unsaponifiable fraction of olive oil in amounts ranging from 50 to 500 mg.

3. The composition according to claim 1, for oral administration comprising per dosage unit:
   a) an extract of *Vitis vinifera* in free form or in the form of a complex with phospholipids, or an extract of *Punica granatum*, in amounts ranging from 50 to 1000 mg;
   b) a lipophilic extract of *Zingiber officinale* in amounts ranging from 10 to 80 mg;
   c) a lipophilic extract of *Zanthoxylum* spp. in amounts ranging from 1 to 50 mg or, alternatively, a lipophilic extract of *Echinacea* spp. or of *Acmella oleracea* in amounts ranging from 5 to 50 mg;
   d) an unsaponifiable fraction of olive oil in amounts ranging from 50 to 500 mg.

4. The composition according to claim 3, comprising:
   a) an extract of *Vitis vinifera* in free form or in the form of a complex with phospholipids, or an extract of *Punica granatum*, in the amount of 200 mg;
   b) a lipophilic extract of *Zingiber officinale* in the amount of 50 mg;

c) a lipophilic extract of *Zanthoxylum* spp. in the amount of 20 mg or, alternatively, a lipophilic extract of *Echinacea* spp. or of *Acmella oleracea* in the amount of 10 mg;
d) an unsaponifiable fraction of olive oil in the amount of 150 mg.

5. The composition according to claim 1 comprising:
a) an extract of *Vitis vinifera* in free form or in the form of a complex with phospholipids, or an extract of *Punica granatum* in amounts ranging from 50 to 1000 mg;
b) a lipophilic extract of *Zingiber officinale* in amounts ranging from 10 to 80 mg; and
c) a lipophilic extract obtained from plants containing polyunsaturated fatty acid isobutylamides selected from the group consisting of *Echinacea* spp. extract, *Zanthoxylum* spp. extract and *Acmella oleracea* extract in amounts ranging from 5 to 50 mg;
d) N-acetylglucosamine in amounts ranging from 50 to 500 mg; or
e) diacerein in amounts ranging from 20 to 200 mg.

6. The composition according to claim 5 comprising
a) an extract of *Vitis Vinifera* in a free form or in the form of a complex with phospholipids, or an extract of *Punica granatum* in the amount of 200 mg;
b) a lipophilic extract of *Zingiber officinale* in the amount of 50 mg;
c) a lipophilic extract of *Zanthoxylum* spp. in the amount of 20 mg or, alternatively, a lipophilic extract of *Echinacea* spp. or of *Acmella oleracea* in the amount of 10 mg;
d) N-acetylglucosamine in the amount of 150 mg; or
e) diacerein in the amount of 50 mg.

7. The composition according to claim 5, comprising:
a) an extract of *Vitis vinifera* complexed with phospholipids in the amount of 200 mg;
b) a lipophilic extract of *Zingiber officinale*, containing 30% w/w of gingerols and shogaols, in the amount of 50 mg;
c) a lipophilic extract of *Zanthoxylum* spp. in the amount of 10 mg;
d) an unsaponifiable fraction of olive oil in the amount of 100 mg; or
e) N-acetylglucosamine in the amount of 150 mg; or
f) diacerein in the amount of 50 mg.

8. The composition according to claim 1, for topical administration comprising:
a) an extract of *Vitis vinifera* complexed with phospholipids in amounts ranging from 0.1 to 2.5% w/w;
b) a lipophilic extract of *Zingiber officinale* in amounts ranging from 0.1 to 1% w/w;
c) a lipophilic extract of *Zanthoxylum* spp. in amounts ranging from 0.1 to 1% w/w;
d) an unsaponifiable fraction of olive oil in amounts ranging from 0.1 to 1% w/w.

9. The composition according to claim 7, comprising:
a) the extract of *Vitis vinifera* complexed with phospholipids in the amount of 1% w/w;
b) the lipophilic extract of *Zingiber officinale* in the amount of 0.5% w/w;
c) the lipophilic extract of *Zanthoxylum* spp. in the amount of 0.5% w/w;
d) the unsaponifiable fraction of olive oil in the amount of 0.5% w/w.

10. The composition according to claim 1, wherein *Punica granatum* extract is characterised by a 40% w/w content of punicalagins.

11. The composition according to claim 1, wherein the lipophilic extract of *Zingiber officinale* is characterised by a 30% w/w content of gingerols and shogaols.

12. The composition according to claim 1, wherein the unsaponifiable fraction of olive oil is characterized by a content in terpenes and polyalcohols ranging from 40 to 90% w/w.

13. The composition according to claim 1 for use in the prevention and/or treatment of inflammation and pain.

14. The composition for use according to claim 13, wherein said inflammation and said pain comprise osteoarticular inflammation, pain, and cartilage damage.

15. The composition for use according to claim 13, wherein said pain is systematic pain or peripheral pain in small and large joints, said joints comprising knee and femoral sockets.

16. The composition for use according to claim 15, wherein said peripheral pain is due to diabetic neuropathy, neuropathy induced by chemotherapy, muscle pains and inflammatory states comprising cutaneous inflammations.

17. A composition comprising:
a) an extract of *Vitis vinifera* in free form or in the form of a complex with phospholipids, or an extract of *Punica granatum* in amounts ranging from 200 to 250 mg;
b) a lipophilic extract of *Zingiber officinale* in the amount of 50 mg;
c) a lipophilic extract obtained from plants containing polyunsaturated fatty acid isobutylamides selected from the group consisting of *Echinacea* spp. extract, *Zanthoxylum* spp. extract and *Acmella oleracea* extract in amounts ranging from 15 to 20 mg;
d) an unsaponifiable fraction of olive oil and/or corn oil in the amount of 150 mg; or
e) N-acetylglucosamine in the amount of 150 mg; or
f) diacerein in the amount of 50 mg.

* * * * *